United States Patent [19]

Sinn

[11] Patent Number: 5,335,783
[45] Date of Patent: Aug. 9, 1994

[54] RETAINER FOR A COMBINED SURGICAL NEEDLE-SUTURE DEVICE

[75] Inventor: Hans-Jurgen F. Sinn, Fairfield, Conn.

[73] Assignee: United States Surgical Corporation, Norwalk, Conn.

[21] Appl. No.: 870,492

[22] Filed: Apr. 16, 1992

[51] Int. Cl.⁵ .............................. A61B 17/06
[52] U.S. Cl. .................. 206/63.3; 206/227; 206/380
[58] Field of Search ............ 206/63.3, 227, 495, 206/380, 382, 388

[56] References Cited

U.S. PATENT DOCUMENTS

| | | |
|---|---|---|
| 3,363,751 | 1/1968 | Shave et al. . |
| 3,444,994 | 5/1969 | Kaepernik et al. . |
| 3,759,376 | 9/1973 | Lisowski . |
| 3,857,484 | 12/1974 | Thyen . |
| 3,939,969 | 2/1976 | Miller et al. . |
| 3,951,261 | 4/1976 | Mandel et al. . |
| 3,985,227 | 10/1976 | Thyen et al. . |
| 4,034,850 | 7/1977 | Mandel et al. ............... 206/63.3 |
| 4,063,638 | 12/1977 | Marwood . |
| 4,089,409 | 5/1978 | Cerwin . |
| 4,120,395 | 10/1978 | Mandel et al. . |
| 4,135,623 | 1/1979 | Thyen . |
| 4,192,420 | 3/1980 | Worrell, Sr. et al. . |
| 4,249,656 | 2/1981 | Cerwin et al. . |
| 4,253,563 | 3/1981 | Komarnycky . |
| 4,284,194 | 8/1981 | Flatau . |
| 4,406,363 | 9/1983 | Aday . |
| 4,412,614 | 11/1983 | Ivanov et al. . |
| 4,413,727 | 11/1983 | Cerwin et al. . |
| 4,427,109 | 1/1984 | Roshdy . |
| 4,483,437 | 11/1984 | Cerwin et al. . |
| 4,491,218 | 1/1985 | Aday . |
| 4,496,045 | 1/1985 | Ferguson et al. . |
| 4,533,041 | 8/1985 | Aday et al. . |
| 4,555,016 | 11/1985 | Aday et al. . |
| 4,572,363 | 2/1986 | Alpern . |
| 4,574,948 | 3/1986 | Huck et al. . |
| 4,574,957 | 3/1986 | Stead . |
| 4,615,435 | 10/1986 | Alpern et al. . |
| 4,708,241 | 11/1987 | Black . |
| 4,813,537 | 3/1989 | Okuhara et al. . |
| 4,884,681 | 12/1989 | Roshdy et al. . |
| 4,887,710 | 12/1989 | Roshdy et al. . |
| 4,896,767 | 1/1990 | Pinheiro . |
| 4,946,043 | 8/1990 | Roshdy et al. . |

FOREIGN PATENT DOCUMENTS

| | | | |
|---|---|---|---|
| 662417 | 4/1963 | Canada | ............... 206/63.3 |
| 1238615 | 4/1967 | Fed. Rep. of Germany | ..... 206/63.3 |
| 78634 | 11/1963 | France | ................. 206/63.3 |

*Primary Examiner*—David T. Fidei

[57] ABSTRACT

A retainer for a combined surgical needle suture device, or armed suture, possesses a cut-away region and integral slot which facilitates loading and removal of the armed suture therefrom.

24 Claims, 6 Drawing Sheets

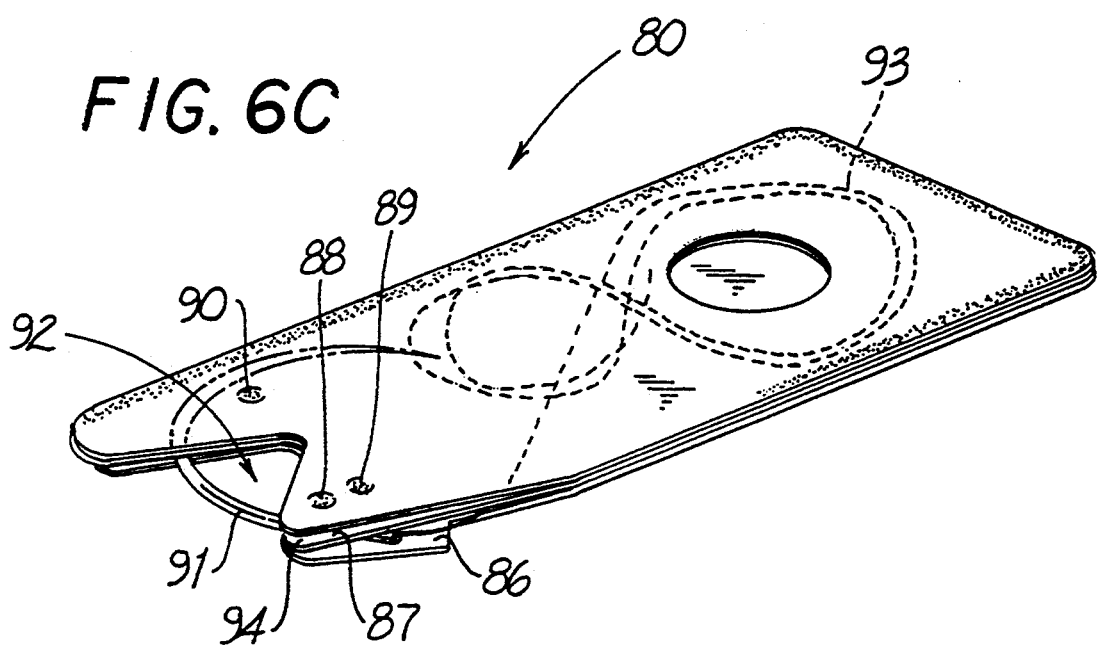

RETAINER FOR A COMBINED SURGICAL NEEDLE-SUTURE DEVICE

BACKGROUND OF THE INVENTION

This invention relates to a retainer for a combined surgical needle-suture device, also commonly referred to as an "armed suture" or simply a "suture", as part of a suture package. Retainers for sutures are known, inter alia, from U.S. Pat. Nos. 3,363,751; 3,444,994; 3,759,376; 3,857,484; 3,939,969; 3,951,261; 3,985,227; 4,063,638; 4,089,409; 4,120,395; 4,135,623; 4,192,420; 4,249,656; 4,413,727; 4,253,563; 4,284,194; 4,406,363; 4,412,614; 4,413,727; 4,427,109; 4,483,437; 4,491,218; 4,496,045; 4,533,041; 4,555,016; 4,572,363; 4,574,948; 4,574,957; 4,615,435; 4,708,241; 4,813,537; 4,884,681; 4,887,710; 4,896,767; and, 4,946,043.

As an essential component of a suture package, the suture retainer should possess good storing qualities, provide safety in handling and permit ready access to, and removal of, the stored sutures.

SUMMARY OF THE INVENTION

By way of meeting the foregoing criteria, there is provided in accordance with this invention a retainer for a combined surgical needle-suture device, the retainer comprising:

a) front and rear panels joined along common edges to provide an enclosure;

b) a cut-out section formed along a portion of at least one edge of the enclosure, the cut-out section providing an open needle access region; and, c) a slot formed along a portion of at least one edge of the enclosure, the slot providing a lateral opening which is continuous with the open needle access region.

The provision of a lateral slot in the retainer of this invention permits an armed suture to be loaded into the retainer suture end first with the needle assuming such a position in the retainer that a portion of it will be partially exposed in the open needle access region. This arrangement results in a highly visible needle display section from which each needle and its attached suture can be easily removed, advantages which are readily appreciated by surgeons and other operating room personnel. Moreover, the retainer of this invention can be mass produced at relatively low cost, particularly when assembled by a sheet or web feed arrangement.

DESCRIPTION OF THE PREFERRED EMBODIMENTS

Figure 1:
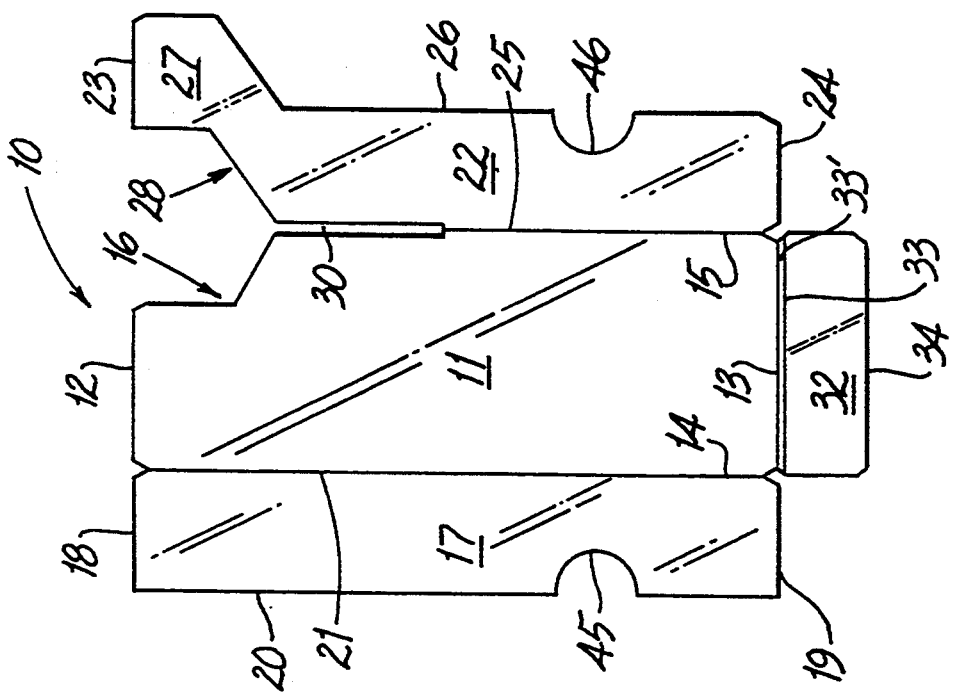
FIG. 1 is a plan view of a first embodiment of an unassembled armed suture retainer blank in accordance with the invention.

As shown in FIG. 1, retainer blank 10 includes a first, or main, panel 11 possessing top and bottom edges 12 and 13, respectively, first and second lateral edges 14 and 15, respectively, and a cut-out region 16 at the juncture of top edge 12 and second lateral edge 15.

A second panel 17 possessing top and bottom edges 18 and 19, respectively, and first and second lateral edges 20 and 21, respectively, is foldably joined to first lateral edge 14 of first panel 11.

A third panel 22 possessing top and bottom edges 23 and 24, respectively, and first and second lateral edges 25 and 26, respectively, is foldably joined to second lateral edge 15 of first panel 11. Lateral extension 27 on third panel 22 will, in the assembled condition of the retainer, be positioned upon or under the adjacent surface of second panel 17 (depending upon whether panel 17 or panel 22 is the first to be folded over), an advantageous feature when sealing the retainer. Third panel 22 features a cut-out region 28 at the junction of top edge 23 and second lateral edge 26 such that in the assembled condition of retainer blank 11, i.e., retainer 10' shown in FIG. 2, cut-out regions 16 and 28 cooperate to form a needle access region 29. The geometries of cut-out regions 16 and 28 can assume various shapes, e.g., curved or arcuate, linear, etc., and can complement each other more or less exactly as shown or they can be slightly different.

A slot 30 is formed along a portion of the juncture of second lateral edge 15 of first panel 11 and first lateral edge 25 of third panel 22 such that in the assembled condition of the retainer blank, the slot provides a lateral opening 31 which is continuous with open needle access region 29.

Completing the retainer blank, a fourth panel 32 is provided which possesses top and bottom edges 33 and 34, respectively. Fourth panel 32 is foldably joined at its top edge 33 to bottom edge 13 of first panel 11, advantageously through a narrow strip 33' which provides a crease to better accommodate the thicknesses of panels 17 and 22 as shown in FIG. 2.

Figure 2:
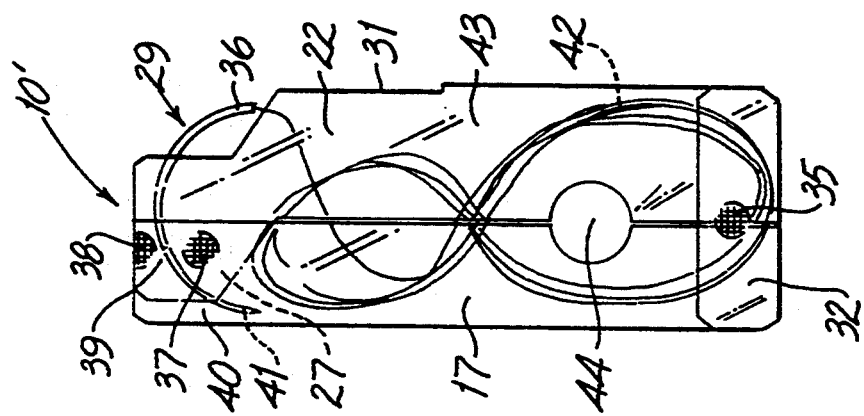
FIG. 2 is a plan view of the filled armed suture retainer assembled from the retainer blank of FIG. 1.

To assemble retainer blank 10 and provide retainer 10' of FIG. 2, second panel 17 is folded over upon first panel 11 and third panel 22 is folded over upon second panel 17 such that extension 27 on third panel 22 lies upon a portion of underlying second panel 17. Finally, fourth panel 32 is folded upon panels 17 and 22 to complete the enclosure. The fourth panel can be maintained in place by any one or several expedients including the use of adhesive, one or more welds such as ultrasonic or radio frequency spot weld 35, and the like. It will, of course, be appreciated that the sequence in which panels 17, 22 and 32 are folded to provide assembled retainer 10' of FIG. 2 can be varied in a number of ways and still provide an enclosure for an armed suture.

In the embodiment of the invention shown in FIG. 2, suture retainer 10' which has been assembled from retainer blank 10 of FIG. 1 is fabricated from a sheet of thermoplastic resin, e.g., polyethylene terephthalate (PET), a spunbonded polyethylene sheet material such as DuPont's Tyvek®, etc. Ultrasonic spot welds 37 and 38 separated by space 39 are formed in the region of extension 27 to secure the opposed interior faces of adjacent panels to each other and to panel 11 and at the same time provide a separate pocket or compartment 40 accommodating the tip region of needle 41. This provision of a pocket for receiving the sharp tip of the needle eliminates the need for a separate "needle park" (usually a small block of foam material into which the needle point can be embedded) thereby reducing the complexity, cost and bulk of the retainer.

Suture 42 can be stored in main body 43 of retainer 10' in any suitable configuration, e.g., the figure-8 pattern shown. When suture 42 is of the cat-gut variety, it is the usual practice to maintain the suture in an alcohol-wetted state. In such case, an aperture 44 formed from semicircular cutouts 45 and 46 on panels 17 and 22, respectively, of retainer blank 10 can be provided as an alcohol-fill port.

Figure 3:
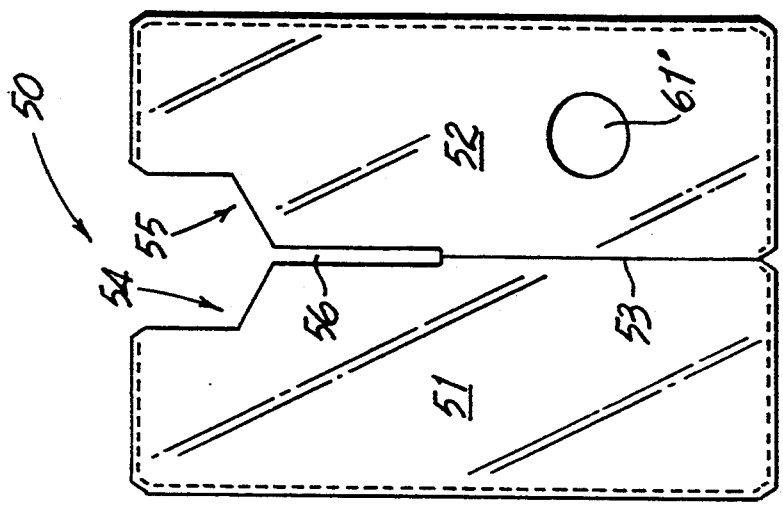
FIG. 3 is a plan view of a second embodiment of an unassembled armed suture retainer blank in accordance with the invention.

Retainer blank 50 illustrated in FIG. 3 represents still another embodiment of the present invention and includes first panel 51 joined to second panel 52 along their common edge 53. When panel 51 is folded over upon panel 52 and their mutually contacting edges sealed, e.g., where indicated in dotted outline, to form the assembled retainer, cut-out regions 54 and 55 and slot 56 form a needle access region and lateral opening corresponding respectively to needle access region 29 and lateral opening 31 of retainer 10' of FIG. 2. Retainer blank 50 can be provided with a single ultrasonic weld as in weld 67 of retainer 60' of FIG. 4C for receiving the sharp point of the suture needle. Aperture 61' can be provided as in alcohol-fill port 44 of retainer 10' of FIG. 2.

Figure 4A:
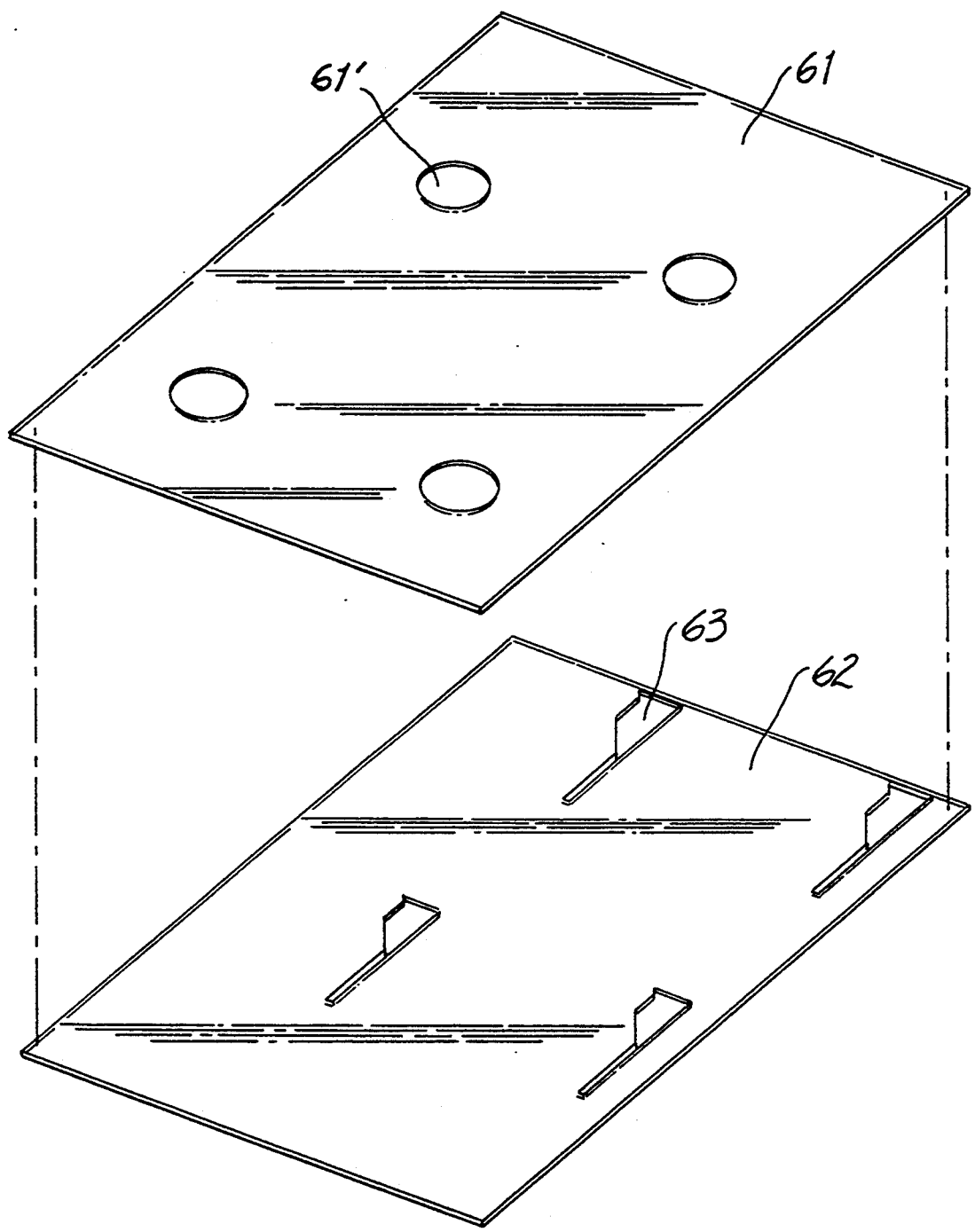
FIGS. 4A-4C illustrate steps in the manufacture of a third embodiment of an armed suture retainer of this invention.
Figure 4B:
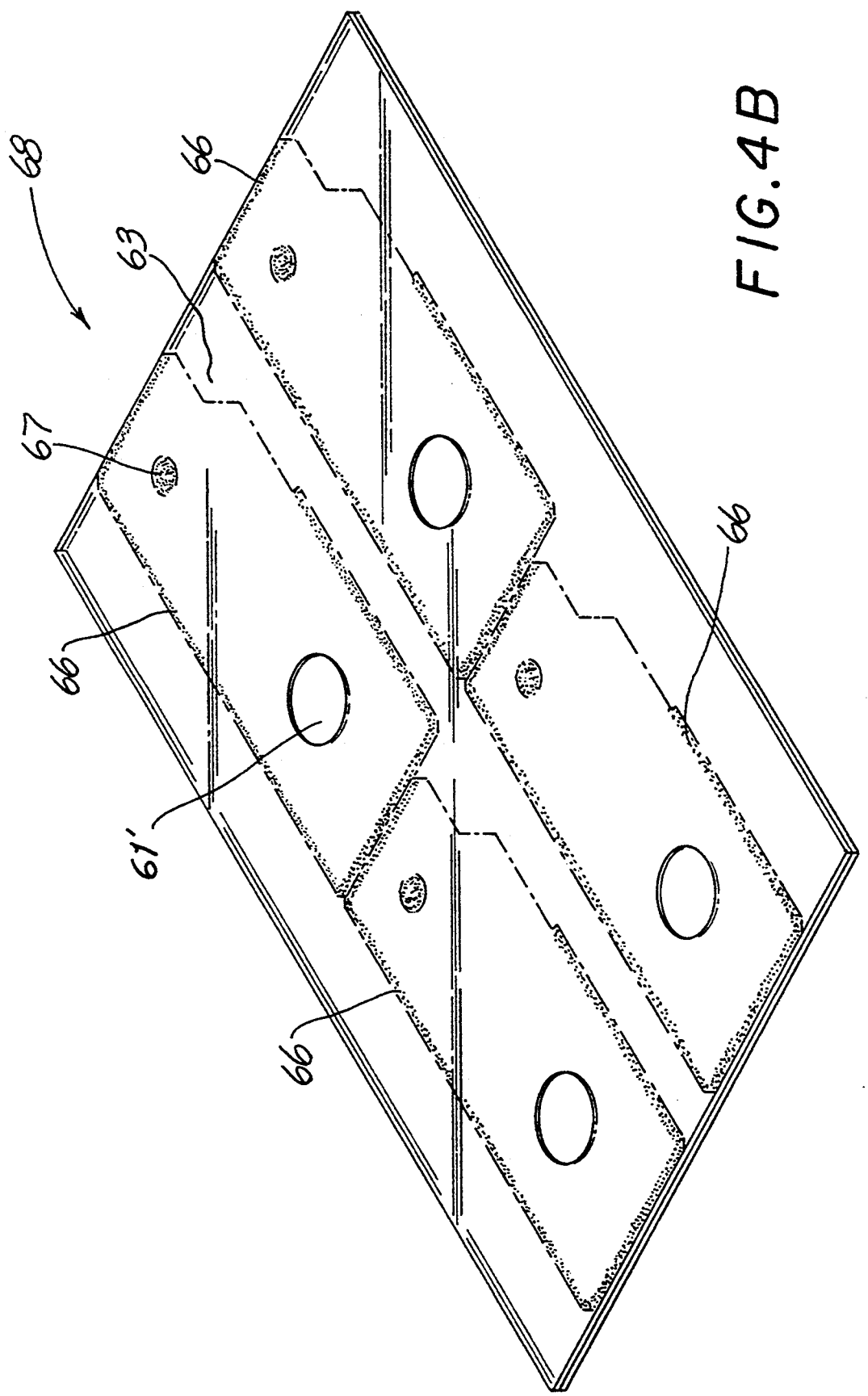
Figure 4C:
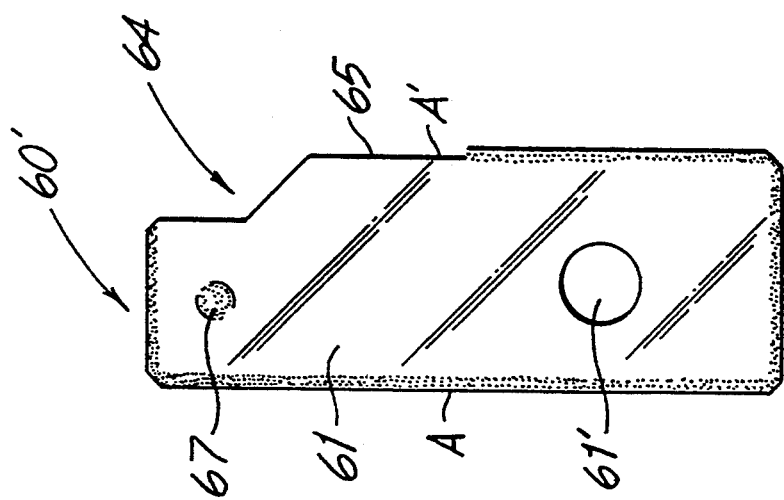

FIGS. 4A-4C describe a sequence of manufacturing operations for providing retainer 60' of FIG. 4C, an embodiment of the invention which is very similar to that formed from retainer blank 50 of FIG. 3, the principal difference between the two being that the former is obtained from a single continuous sheet and the latter is obtained from two separate sheets. As shown in FIG. 4A, sheet 61 possessing a number of alcohol-fill ports 61' is precisely aligned with underlying sheet 62 possessing a like number of cut-out regions 63 having a configuration and arranged in a pattern which will ultimately provide needle access region 64 and lateral opening 65 in each of the finished armed suture retainers 60' of FIG. 4C cut from the assembled sheets. Aligned sheets 61 and 62 are shown placed together to form double-layered sheet 68 of FIG. 4B. Ultrasonic welding or adhesive joins the sheets to each other in the regions indicated by stippling 66 and spot welds 67 are provided to form needle-receiving pockets. Finally, precision cutting of sheet 68 produces identical retainers as in representative retainer 60' of FIG. 4C.

Figure 5:
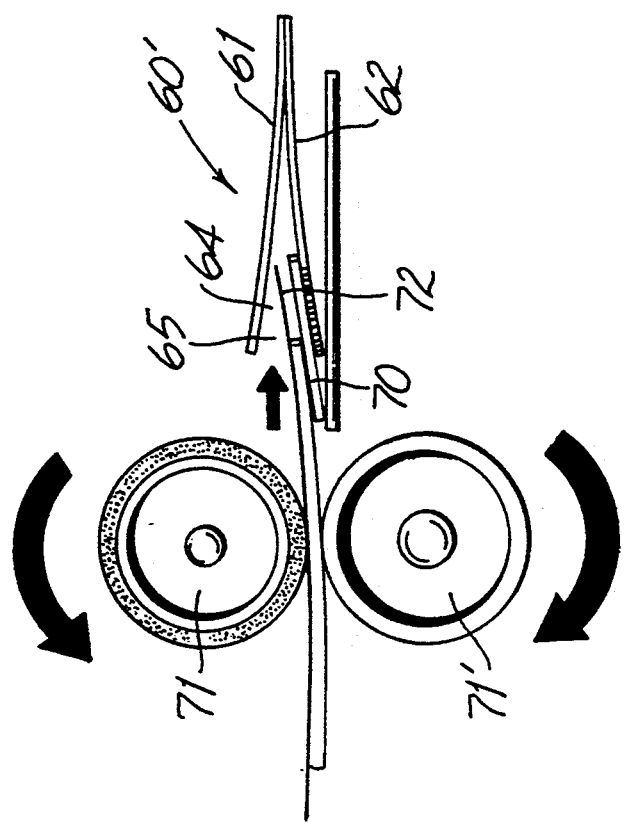
FIG. 5 illustrates a suture loading operation suitable for filling the armed suture retainer herein; and, FIGS. 6A-6C illustrate steps in the manufacture of a fourth embodiment of an armed suture retainer in accordance with the invention.

FIG. 5 illustrates a convenient method for filing any of the various embodiments of suture retainer of this invention with a suture and will be described in connection with retainer 60' of FIG. 4C. After panel 61 has been spread somewhat apart from panel 62 in the region of needle access region 64 and lateral opening 65 (corresponding to line A—A' of FIG. 4C), advantageously employing angled spreader 70 to facilitate and maintain their being spread apart, counter-rotating friction wheels 71 and 71' grip free end 72 of an armed suture and pass the suture into the retainer where it tends to assume a figure-8 configuration.

Figure 6A:
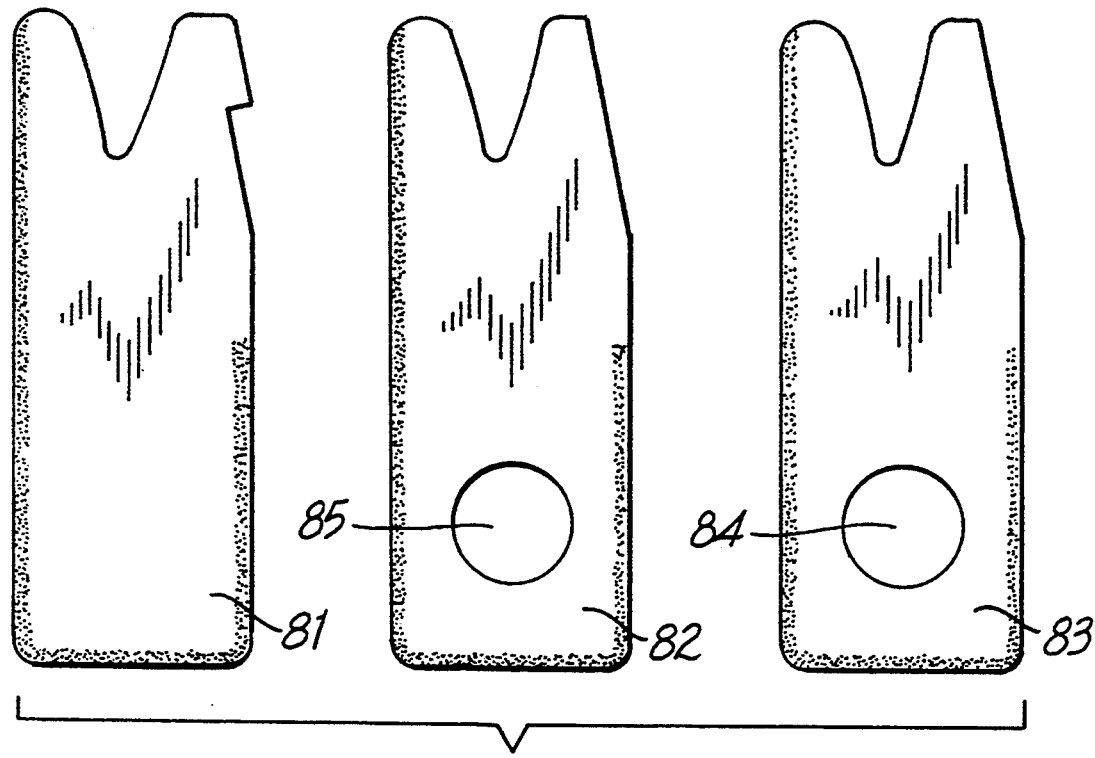
Figure 6B:
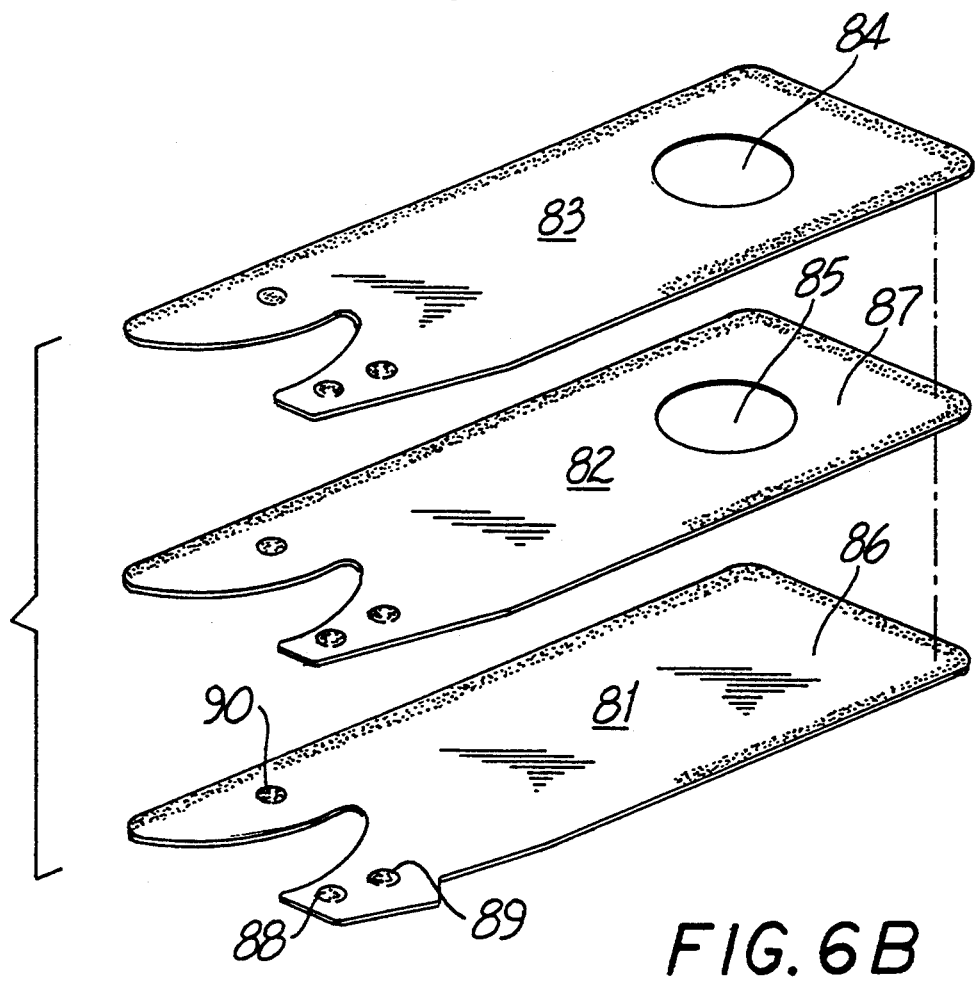

FIGS. 6A, 6B and 6C illustrate the assembly of yet another embodiment of suture retainer in accordance with the invention, retainer 80 which is assembled from three panels 1, 82 and 83 so as to provide two separate superimposed enclosures (FIG. 6C), a lower enclosure 86 for the needle component and an upper enclosure 87 for the suture component of a combined surgical needle-suture advise. This two-tier packaging arrangement eliminates the possibility of the needle entangling or snarling the suture.

Front panel 83, rear panel 81 and middle panel 82 can be constructed from the same or different materials. A preferred material for the panels, particularly when the assembled retainer is used for the wet (alcohol) packaging of a suture is a spunbonded polyethylene sheet material such as DuPont's Tyvek®. The surfaces of such material exhibit relatively low coefficients of friction, can be easily spot welded, e.g., in the pattern shown by the stippling to secure the panels to each other and to provide frangible welds for holding the needle component in place, and is better at holding the packaging fluid than, say, a polyethylene terephthalate sheet material. Fill holes 84 and 85 can be provided to receive a dose of packaging fluid during the filling operation. In the fully assembled and filled retainer 80 of FIG. 6C, needle 91 (partly shown in dotted outline) occupies lower enclosure 86 where it is held in place by three spot welds 88, 89 and 90 and suture 93 (largely shown in dotted outline) occupies upper enclosure 87 where it assumes an approximate figure-8 configuration as in the other retainers herein. To remove the armed suture needle 91 is gripped with a needle clamp where exposed by cut-out section 92 and pulled away from retainer 80, the needle breaking through frangible spot weld 88 as a result of the pulling force. Suture component 93 is easily withdrawn from retainer 80 through the lateral opening provided by slot 94.

What is claimed is:

1. A retainer for a combined surgical needle-suture device, the retainer comprising:
    a) front and rear panels joined along common edges to provide an enclosure, said front and rear panels each possessing a top edge and at least one side edge at least a portion of which is generally orthogonal to said top edge, wherein said front and rear panels are joined by a weld positioned in such a manner as to provide a separate compartment within the enclosure for receiving the pointed section of a surgical needle;
    b) a cut-out section formed along a portion of said top edge of the enclosure, the cut-out section providing an open needle access region; and,
    c) a slot formed along a portion of said side edge of the enclosure, the slot providing a lateral opening which is continuous with the open needle access region.

2. The retainer of claim 1 formed from a synthetic resin.

3. The retainer of claim 1 formed from a transparent synthetic resin.

4. The retainer of claim 1 formed from polyethylene terephthalate.

5. The retainer of claim 1 formed from a spunbonded polyethylene sheet material.

6. The retainer of claim 1 possessing a separate opening for admission of liquid to the interior of the retainer.

7. A retainer for a combined surgical needle-suture device, the retainer comprising:
    a) a first panel possessing top and bottom edges and first and second lateral edges, the first panel possessing a cut-away region at the juncture of its top and second lateral edges;
    b) a second, inwardly folded panel possessing top and bottom edges and first and second lateral edges, the second lateral edge of the second panel being joined to the first lateral edge of the first panel;

c) a third, inwardly folded panel possessing top and bottom edges and first and second lateral edges, the first lateral edge of the third panel being joined to the second lateral edge of the first panel, the third panel possessing a cut-out region at the junction of its top and first lateral sides which cooperates with the cut-out region of the first panel to form an open needle access region, the first lateral edge of the second panel meeting with or extending beyond the second lateral edge of the third panel;

d) a slot formed along a portion of the juncture of the second lateral edge of the first panel and the first lateral edge of the third panel, the slot providing a lateral opening which is continuous with the open needle access region; and, e) a fourth, inwardly folded panel possessing top and bottom edges and first and second lateral sides, the top edge of the fourth panel being joined to the bottom edge of the first panel.

8. The retainer of claim 7 wherein the third panel possesses a laterally extending portion which overlaps or underlies a portion of the second panel.

9. The retainer of claim 7 formed from a synthetic resin.

10. The retainer of claim 7 formed from a transparent resin.

11. The retainer of claim 7 formed from polyethylene terephthalate.

12. The retainer of claim 7 formed from a spunbonded polyethylene sheet material.

13. The retainer of claim 7 possessing a separate opening for admission of liquid to the interior of the retainer.

14. The retainer of claim 7 wherein the closed condition of the retainer is maintained by one or more welds joining the first panel to the second and/or third panels.

15. The retainer of claim 14 wherein a weld is positioned in such manner as to provide a separate compartment within the interior of the retainer for receiving the pointed section of a surgical needle.

16. The retainer of claim 7 wherein the second, third and fourth panels are joined to the first panel through narrow expansion panels.

17. A retainer blank especially adapted for assembly into a retainer for a combined surgical needle-suture device, the retainer blank comprising:

a) a first panel possessing top and bottom edges and first and second lateral edges, the first panel possessing a cut-out region at the juncture of its top and second lateral edges;

b) a second panel possessing top and bottom edges and first and second lateral edges, the second lateral edge of the second panel being foldably joined to the first lateral edge of the first panel;

c) a third panel possessing top and bottom edges and first and second lateral edges, the first lateral edge of the third panel being foldably joined to the second lateral edge of the first panel, the third panel possessing a cut-out region at the juncture of its top and first lateral edges such that in the assembled condition of the retainer blank, the cut-out regions of the second and third panels cooperate to provide an open needle access region;

d) a slot formed along a portion of the juncture of the second lateral edge of the first panel and the first lateral edge of the third panel such that in the assembled condition of the retainer blank, the slot provides a lateral opening which is continuous with the open needle access region; and, e) a fourth panel possessing top and bottom edges and first and second lateral sides, the top edge of the fourth panel being foldably joined to the bottom edge of the first panel.

18. The retainer blank of claim 17 wherein the third panel possesses a laterally extending portion such that in the assembled condition of the retainer blanks, the laterally extending portion will overlap or underlie a portion of the second panel.

19. The retainer blank of claim 17 formed from a synthetic resin.

20. The retainer blank of claim 17 formed from a transparent synthetic resin.

21. The retainer blank of claim 17 formed from polyethylene terephthalate.

22. The retainer blank of claim 17 formed from a spunbonded polyethylene sheet material.

23. The retainer blank of claim 17 possessing separate opening for admission of liquid to the interior of the assembled blank.

24. The retainer blank of claim 18 wherein the second, third and fourth panels are joined to the first panel through narrow expansion panels.

* * * * *